United States Patent [19]

Mattei et al.

[11] 4,439,420

[45] Mar. 27, 1984

[54] ABSORBABLE HEMOSTATIC COMPOSITION

[75] Inventors: Frank V. Mattei, Piscataway, N.J.; Martin Stephenson; Allin K. Gordon, both of Peterborough, Canada; Namassivaya Doddi, Upland, Calif.

[73] Assignee: Ethicon, Inc., Somerville, N.J.

[21] Appl. No.: 442,219

[22] Filed: Nov. 16, 1982

[51] Int. Cl.$^3$ ...................... A61K 31/23; A61K 31/74
[52] U.S. Cl. ...................... 424/78; 424/289; 424/312; 424/318; 424/339
[58] Field of Search .......................... 424/312, 318, 78

[56] References Cited

U.S. PATENT DOCUMENTS

| | | | |
|---|---|---|---|
| 2,772,999 | 12/1956 | Masci et al. | 167/84 |
| 3,395,217 | 7/1968 | Statt | 424/81 |
| 4,186,448 | 2/1980 | Brekke | 128/296 |
| 4,201,216 | 5/1980 | Mattei | 128/335.5 |

FOREIGN PATENT DOCUMENTS 1584080 2/1981 United Kingdom .

OTHER PUBLICATIONS

Annals of Surgery, vol. 132, 1950, pp. 1128–1130, New Absorbable Hemostatic Bone Wax, Drs. Geary and Frantz.
Chemical Abstracts 82:46252e; 1975 (Gupta et al.).
Chemical Abstracts 85:161435r; 1976 (Yates et al.).

*Primary Examiner*—Leonard Schenkman

[57] ABSTRACT

An absorbable hemostatic composition for use in the control of osseous hemorrhage, comprising a biocompatible fatty acid salt in a biocompatible base, said composition having a putty-like consistency at room temperature. The preferred composition is one in which the fatty acid salt is calcium stearate.

22 Claims, No Drawings

ABSORBABLE HEMOSTATIC COMPOSITION

BACKGROUND OF THE INVENTION

1. Field of the Invention

This invention relates to a bone sealant and more particularly to an absorbable hemostatic composition, comprising a biocompatible fatty acid salt in a biocompatible base, the composition having a putty-like consistency at room temperature. This invention also relates to a process for applying the bone sealant.

2. Description of Prior Art

Various substances and compositions have been employed by members of the medical profession to control bleeding from cut bone surfaces. One class of materials used for the control of this type of hemorrhage is called bone wax. Bone waxes are used for the purpose of controlling hemorrhages from the cut surfaces of bones, such as those of the skull, by forcibly smearing the wax over the cut surface so that the material acts mechanically to occlude and seal the open ends of the bleeding osseous vessels and sinuses.

Bone waxes used in surgery today are generally prepared from refined beeswax which has been admixed with other nonabsorbable and water insoluble hydrocarbons and vegetable oils. Certain disadvantages inhere in these bone wax compositions, as for example, relatively poor adhesion properties, and the hard brittle state of the wax at room temperatures requiring use at elevated temperatures. Furthermore, paraffin based commercial bone wax is not absorbed by the body and thus remains at the site of application for long periods of time. As a result the wax acts as a foreign material, tending, in some instances, to make it difficult for the body to fight infection and inflammatory reactions that may be introduced in the surrounding tissue, and it also interferes with bone regrowth.

In order to overcome the latter problem, British Pat. No. 1,584,080 discloses an absorbable hemostatic bone sealant, which contains the active components collagen and fibrin. However, the composition of British Pat. No. 1,584,080 suffers from the disadvantage that its storage conditions must be controlled in order to retain desirable aesthetic and tactile properties since biological materials of animal origin are used.

U.S. Pat. No. 3,395,217 discloses nonabsorbable bone wax compositions comprised of low molecular weight ethylene copolymer waxes containing from about 15 to about 40 percent by weight of another unsaturated consituent and having molecular weights in the range of 1000 to 4000. These waxes have a semisolid consistency such that they can be kneaded between the fingers when at room temperature and have the right amount of tack and adhesion so that they can be easily manipulated in the hands of the surgeon or applied by any suitable applicator such as a gloved finger, spatula or appropriate disposable applicator.

U.S. Pat. No. 2,722,999 describes an absorbable bone wax comprised of a water soluble innocuous base and free acid cellulose glycolic acid ether or free acid cellulose hydroxypropionic acid ether as a hemostatic agent. The composition also preferably contains a tackifier such as cellulose glycolic acid ether salt or cellulose hydroxypropionic acid ether salt (preferably sodium salt) and water as a plasticizer. It is to be noted that cellulose and its derivatives are generally not biologically degradable, but merely soluble, and if the molecular weights are high enough, may not even pass through the kidneys.

The Annals of Surgery 132, 1128 (1950) describes an absorbable hemostatic bone wax containing powdered oxidized cellulose as the hemostatic agent in a base of polyethylene glycol. The base is a mixture of high and low molecular weight polyethylene glycols selected to provide the malleability and consistency of material desired for this application. However, polyethylene glycols are completely water soluble. When they comprise the largest percentage of the mixture, the mixture becomes slimy in the area wet with tissue fluids, this being true of any water soluble base. In addition, some polyethylene glycols give a pronounced tissue reaction.

U.S. Pat. No. 4,186,448 discloses a one-piece molded body member for filling and covering a bone void or soft tissue deficiency, which body member attracts blood in fluid suspension by capillary action until clotting forms which ultimately leads to the formation of tissue and/or bone. The body member is made of a biodegradable material such as polylactic acid.

The present invention provides a new absorbable bone sealant which is a putty-like semisolid at room temperature. The softness of the sealant allows the material to be packaged in a syringe, plastic or coated paper envelope, or aluminum or glass tube from which it may be extruded or dispensed in desired amounts during use. The sealant has sufficient tack so that it adheres to bone surfaces, yet is easily manipulated in the hands of the surgeon without crumbling or sticking to the surgeon's gloves.

In accordance with expectations based on prior experience, the preferred fatty acid salt of the present invention, calcium stearate, would have been expected to remain as a separate phase after having been mixed with an oil. It has been found, surprisingly, in accordance with the present invention, that when calcium stearate is heated with castor oil (or other biocompatible bases mentioned herein), there is produced a gelatinous product having a translucent appearance with a waxy consistency, particularly suitable as a bone sealant. Furthermore, the compositions of the present invention also possess the advantage of not "setting-up" even after a long period of standing and they also maintain an aesthetic physical appearance. Also, they can be sterilized by radiation without affecting their properties. Thus, the appropriate consistency, set-up, smearability and translucency (which are desirable properties in a bonewax) are to be found in the sealant of the present invention. Furthermore, calcium stearate is known to be completely absorbable in the body (see U.S. Pat. No. 4,201,216, wherein a coating, which is about 50% calcium stearate, is applied to synthetic absorbable sutures). In addition to being absorbable, the compositions of the present invention also demonstrate a low level of tissue reaction.

SUMMARY

The bone sealant composition of the present invention comprises (i) a component (A) comprising either a biocompatible fatty acid salt alone which comprises between 45% to 80% by weight (based on the weight of the total composition); or a mixture of said fatty acid salt with a biocompatible in vivo absorption enhancing agent in which said mixture comprises between 35% and 45% by weight of said fatty acid salt (based on the weight of the total composition) and between 25% and 35% by weight of said absorption enhancing agent (based on the weight of the total composition); and (ii) a component (B) comprising a biocompatible base.

The cation of the fatty acid salt is selected from the group consisting of calcium, magnesium, zinc, aluminum, lithium, and barium, the fatty acid anion being saturated or unsaturated and containing from 10 to 22 carbon atoms in the chain. This composition has a putty-like consistency at room temperature, and a tackiness sufficient for it to adhere readily to a bloody bone surface. This permits a surgeon to spread the sealant with his fingers or a spatula over the cut surface of a bone and at the same time the sealant will adhere to the bone surface.

The sealant has a consistency of a semisolid which is extrudable from a large orifice syringe. The sealant is packaged in a syringe, plastic envelope or aluminum tube and sterilized by high energy radiation. During use, small amounts of the sealant may be extruded from the package as required by the surgeon. The sealant is effective to control osseous hemorrhage from cut bone and does not interfere with subsequent healing and rejoining of bone parts.

DESCRIPTION OF PREFERRED EMBODIMENTS

The composition of the present invention consists preferably of calcium stearate in a biocompatible base, a preferred base being castor oil. The composition optionally includes an agent for enhancing in vivo absorption, a preferred agent in this connection being dextran. Other suitable biocompatible bases are triglycerides that are known to be metabolizable (as well as fatty acid esters such as isopropyl palmitate known as Deltyl Prime), which glycerides or esters impart desirable organoleptic characteristics and which are nontoxic and nonirritating. In this connection, suitable triglycerides are: sesame oil, almond oil, castor oil, cottonseed oil, corn oil, olive oil, cod liver oil, safflower oil, and soya oil. Other suitable bases are ethylene oxide/propylene oxide block copolymers (known by the trademark Pluronic), polyethylene glycols and methoxy polyethylene glycols (known by the trademark Carbowax). In general, although the above discussed bases are preferred, any biocompatible base which consists of a natural or synthetic oil or wax may be used provided that the composition of fatty acid salt plus base has a putty-like consistency at room temperature and also has a tackiness sufficient for it to adhere readily to a bloody bone surface. When component (A) consists of a fatty acid salt alone, up to 40% by weight of water (based upon the total weight of the composition) may also be added if desired. In such event, the oil or wax base should be present in a weight percent of at least 15% (based on the weight of the total composition).

When component (A) consists of a fatty acid salt plus an absorption enhancing agent, up to 10% by weight of water (based on the weight of the total composition), may be added. In such event, at least 20 weight % of the oil or wax base should be present (based on the weight of the total composition).

The preferred component (A) is calcium stearate. However, fatty acid anions other than the stearate anion may be used. These anions may be saturated or unsaturated and may contain from 10 to 22 carbon atoms in the chain. An example of a suitable unsaturated fatty acid anion is that derived from oleic acid. It should be noted that unnatural fatty acid anions such as the undecylenate are also suitable. Commercial calcium stearate which is suitable for use in the present invention contains up to 33% of calcium palmitate. It should further be noted, that the myristate (which contains 14 carbon atoms in the chain) is also suitable for use in the present invention.

One desirable composition of the present invention consists of calcium stearate in a castor oil base, in which the calcium stearate comprises between 55% and 70% by weight of the composition (a preferred composition containing approximately 60% by weight of calcium stearate). The most preferred in vivo absorption enhancing agent is dextran; and a preferred composition in this connection comprises between 35% and 45% by weight of calcium stearate (based on the weight of the total composition); between 25% and 35% by weight of dextran (based on the weight of the total composition), the remainder being castor oil. A preferred composition comprises about 41 weight % calcium stearate, about 30 weight % dextran and about 29 weight % castor oil.

It is also desirable to add water to the above three ingredients. This reduces the slight granular handling quality of dextran when a thin film of the composition containing same is rubbed between bare fingers. The resultant composition comprises about 38 weight % calcium stearate, about 28 weight % dextran, about 27 weight % castor oil and about 7 weight % water.

Other desirable hemostatic compositions of the present invention, comprise from 45% to 80% by weight of calcium stearate, and a biocompatible base consisting of isopropyl palmitate, sesame oil, almond oil, castor oil, ethylene oxide/propylene oxide block copolymers, polyethylene glycols or methoxy polyethylene glycols.

Applicant has found that compositions of the invention containing a castor oil base, exhibit good adherence to bone, being better in this regard than other compositions of the invention utilizing certain of the other bases.

In order to homogenize the present compositions, a solution of the components, involving little or no chemical change is desirable. The first method of doing so would be to stir a molten liquid of the components. Overall this method is relatively unsuccessful, since the oily emulsion, present during heating, tends to be followed by a phase separation.

A second, more successful method, consists of mechanical mixing by means of mortar and pestle. By means of this method of mechanical mixing, the proper consistency, set-up and smearability are attained. When preparing the mixture, it is preferred to utilize calcium stearate having a particle size of under 100 microns, but more preferably between 10 and 20 microns. Applicant has found that the compounding process is aided by heating the emollient (preferably for about 30 minutes in a 70° C. oven) prior to mixing and then heating the mixture (overnight in a 70° C. oven). On an industrial scale the mixing process may be carried out using a dough mixer or some means of applied pressure (i.e. piston action). A three roll mill of the type used to disperse pigments in protective coatings would be ideal. The customary steel rolls should be replaced with porcelain or other ceramic materials.

Mixtures Gelatinized by Heating

An emollient may be incorporated in the instance wherein the latter gelatinizes with calcium stearate upon heating. The effect is probably due to partial dissolution of the stearate and establishment of a dissolved-/undissolved equilibrium both of solid in liquid and liquid in solid as well. Isopropyl palmitate forms such a gel and a typical composition is prepared by mixing about 35 parts of isopropyl palmitate with about 65 parts of an edible grade of calcium stearate. This is heated to about 150° C. while stirring with a spatula for about 15 to 20 minutes. A transition from opaque white to opalescent/translucent occurs after heating and is maintained in the cooled (room temperature) mixture. Upon cooling, a somewhat "set-up" consistency is formed which very quickly gives way to a desirable workability by hand. When cooled, the surface acquires a very shiny glaze, somewhat suggestive of a true solution at the surface. No oily separation occurs upon standing. In certain instances, upon standing at room temperature overnight, the translucency of the above calcium stearate/isopropyl palmitate gel, reverts back to opacity. Reheating to 150° C. restores the translucency. Occasionally, a mixture will result in a continual return to opacity even after repeated heating. However, a number of gels prepared by Applicant and stored in beakers for over a year still retained their original translucent appearance. When it was attempted to prepare gelatinized mixtures of calcium stearate with either sesame or almond oil, they did not gelatinize as readily or as smoothly as did the mixtures of calcium stearate and isopropyl palmitate. It will thus be seen that different methods of mixing the compounds ought to be selected, according to the nature of the components.

Applicant has found that when calcium stearate is mixed with isopropyl palmitate (preferably in a ratio of 64:36 by weight) using mortar and pestle, this results in a putty-like mass having the consistency desirable in a bone wax. The color, however, is opaque white rather than opalescent/translucent which would be encountered in the instance wherein gelatinization by heat is possible.

Using the mortar and pestle method, however, allows viable mixtures to be prepared from many more candidates than is possible by heating alone. Thus, mixtures whose handworkability properties are quite desirable, may be prepared by mortar and pestling calcium stearate (roughly in the ratio of 64:36 by weight) with either sesame oil, castor oil, Carbowax 400 or Pluronics F68 and water. A dough mixer or a 2 or 3 roll mill (as used in grinding paint or rubber and vinyl compositions) would be ideal for preparing such mixtures. In the latter instance, heat as well as grinding could be applied. Wherever heating shows evidence of creating an equilibrium between dissolved/undissolved phases (as in the gelatinized compositions), this may contribute towards greater stability and less separation of phases by reducing the fugitivity of the oily component.

In Vivo Absorption

Preliminary tests in animals have demonstrated minimal tissue reaction with a mixture such as calcium stearate and sesame oil or castor oil. (See Table 4) Using radio isotopes, it has been found that calcium stearate, in vivo, on its own, is 85% absorbed after fourteen days. However, when calcium stearate is mixed with a second component which is also hydrophobic, such as a triglyceride oil, the hydrophobic barrier which is established and presented to the surrounding tissues may extend the absorption time beyond ninety days, in spite of the fact that both components are absorbable individually. The hydrophobicity may be reduced by incorporating a small percent of a hydrophile which acts as an in vivo absorption enhancing agent (for example, Carbowax, Pluronics, glycerine or propylene glycol). When dextran is incorporated as the third and hydrophilic component, it reduces the hydrophobic barrier and encourages the infiltration of host tissue cells, thus contributing towards faster absorption. Alternatively, the porosity may be maintained by using a small percentage of the total calcium stearate in a coarser form. In this connection, the porosity (due to the particulate nature of calcium stearate) normally would be considered to help invading cells to obtain a foothold and thus be instrumental in absorption). Such porosity may also be maintained by incorporating a small percentage of an absorbable polymer such as a fiber or a grit (for example, catgut powder) or an absorbable inorganic material such as calcium sulfate, into the calcium stearate/oil mixture.

Table 1 sets forth consistency and tactile properties of the instant compositions. It will be noted from Table 1 that the calcium stearate-sesame oil composition and the calcium stearate-almond oil composition provide the most desirable properties of those compositions listed in the Table. Applicant has also found that sterilization with high energy radiation from a Cobalt-60 source, generally has no adverse effect on the consistency and tactile properties of most of the compositions of Table 1. Nevertheless, the effect of sterilization with Cobalt-60 on the compositions of the present invention, is shown in Table 2.

In Vivo Studies

Tissue reaction and efficacy studies were carried out as summarized in the following Tables 3, 4 and 5. The tests were carried out in rats to determine the tissue reaction evoked by the various materials. Three rats were used per sample and the material was either implanted or injected into the ventral subcutis. If the material was solid, approximately 1 cm by 1 cm squares were implanted; if the material was in the form of granules or powder, two scoopfuls, using a small flat spatula were placed in a subcutaneous pocket; and if the materials were liquid, 0.25 mls of the liquid were injected into the subcutis. The rats were examined after 24 hours and usually one rat was killed at this time. The remaining rats were observed for seven days, whereafter they were killed. The implant sites were then exposed and characterized. These characterizations are set forth in Tables 3, 4 and 5.

As will be noted from Table 3, after seven days, essentially none of the single components gave evidence of irritation. However, this is not true of the observations at 24 hours, which vary more widely. As will be noted from Table 4, the two compositions based upon Deltyl Prime or sesame oil, exhibited no adverse tissue reaction, while the remaining two had unfavorable reactions. It should be noted, however, that Carbowax 400 was reported as having no adverse tissue reaction when injected individually; however, as a component of bone wax the reaction was pronounced.

Studies concerning intramuscular absorption of certain bone sealant implants are summarized in Table 6. The formulation of 60% calcium stearate and 40% castor oil by weight showed superior wet handling properties. However, in such formulation, the castor oil retarded absorption and break-up of the calcium stearate implant because of its water repellent nature. It is to be noted that twelve weeks passed before the implant was gone. The formulation which contained 41.4% calcium stearate, 30% dextran and 28.6% castor oil by weight, demonstrated relatively fast absorption. Thus, substantial cell ingrowth into the implant was evident after one week in vivo, implant breakup due to cell ingrowth occurred after two weeks in vivo, and after four weeks in vivo only small areas of tissue reaction were evident in the implants. The four week implants only showed areas of inflammatory cells with a few circular areas present which were most probably fat cells.

Also included within the scope of the present invention is the process for the control of bleeding from cut bone surfaces, which comprises applying to the cut bone surface, the hemostatic composition comprising (i) a component (A) comprising either a biocompatible fatty acid salt alone which comprises between 45% and 80% by weight (based on the weight of the total composition); or a mixture of said fatty acid salt with a biocompatible in vivo absorption enhancing agent in which said mixture comprises between 35% and 45% by weight of said fatty acid salt (based on the weight of the total composition) and between 25% and 35% by weight of said absorption enhancing agent (based on the weight of the total composition); and (ii) a component (B) comprising a biocompatible base.

The cation of said fatty acid salt is selected from the group consisting of calcium, magnesium, zinc, aluminum, lithium and barium, the fatty acid anion being saturated or unsaturated and containing from 10 to 22 carbon atoms in the chain, said composition having a putty-like consistency at room temperature, and tackiness sufficient for it to adhere readily to a bloody bone surface.

The present process is preferably carried out utilizing a composition in which the base is selected from the group consisting of isopropyl palmitate, sesame oil, almond oil, castor oil, ethylene oxide/propylene oxide block copolymers, polyethylene glycols and methoxypolyethylene glycols.

The present process is most preferably carried out utilizing a composition in which component (A) is calcium stearate plus dextran and the base is castor oil. Up to 10% by weight of water (based on the weight of the total composition) may be added, provided at least 20% by weight of castor oil is present (based on the weight of the total composition).

A preferred composition used in this process is one in which the proportions are about 41% by weight calcium stearate, about 30% by weight dextran and about 29% by weight castor oil.

When water is added, a desirable composition used in this process, comprises about 38 weight % calcium stearate, about 28 weight % dextran, about 27 weight % castor oil and about 7 weight % water.

The following examples are provided to further illustrate embodiments of the present invention.

EXAMPLE 1

Mixture of Calcium Stearate and Isopropyl Palmitate Gelatinized by Heating

Thirty-five parts by weight of isopropyl palmitate is mixed with 65 parts by weight of an edible grade of calcium stearate (free of the chick edema factor). The mixture is then heated to about 150° C. while stirring with a spatula for about 15 to 20 minutes. A transition from opaque white to opalescent/translucent occurs after heating and is maintained in the cooled (room temperature) mixture. Upon cooling, a somewhat "set-up" consistency is formed which very quickly gives way to a desirable workability by hand. When cooled, the surface acquires a very shiny glaze. No oily separation occurs upon standing.

EXAMPLE 2

Mixture of Calcium Stearate and Isopropyl Palmitate by Mortar and Pestling

Sixty-four parts by weight of an edible grade of calcium stearate is mixed with 36 parts by weight of isopropyl palmitate and the mixture is then mortared and pestled for about 15 minutes. This results in a desirable putty-like mass having the consistency desirable in a bone wax. The color, however, is opaque white, rather than opalescent/translucent, such as that prepared in accordance with the process of Example 1.

TABLE 1

ABSORBABLE BONE WAX
Consistency & Tactile Properties of Calcium Stearate Based Compositions*

| | Composition, % Wt. | | | | |
|---|---|---|---|---|---|
| | Calc. Stear. **64 Deltyl Prime 36 | Calc. Stear. 65 Almond Oil 35 | Calc. Stear. 63 Sesame Oil 37 | Calc. Stear. 64.25 Carbowax 400 45.75 | Calc. Stear. 48 Pluronic F68 20 H₂O 32 |
| Means of Mixing | | | Mortar and Pestle | | |
| Consistency | smooth soft spongy, less sticky than Pluronic | smooth soft | smooth soft | smooth soft dough-like | smooth, soft sticky, spongy airy |
| Appearance | white, opaque | off-white, semi-translucent | off-white, semi-translucent | white, opaque | white, opaque |
| Greasiness | v. slightly | waxy | waxy | slightly oily | N.A. dries on hand when smeared thin |
| Smearability | v. good | v. good | v. good | v. good | N.A. dries on hand when smeared thin |
| Odor | none | none | none | slight | none |
| Relative Rating*** based on physical properties | 4 | 1 v. similar | 1 | 3 | 2 |
| Viscosity Shear Rate 228.5 Temp. 35° C. | 1911 | | 2372 | 3427 | Begin 225, 369 End 179, 241 Temp. Rise to 36° C. |

TABLE 1-continued

ABSORBABLE BONE WAX
Consistency & Tactile Properties of Calcium Stearate Based Compositions*

| | | | Composition, % Wt. | | |
|---|---|---|---|---|---|
| | Calc. Stear. **64<br>Deltyl Prime 36 | Calc. Stear. 65<br>Almond Oil 35 | Calc. Stear. 63<br>Sesame Oil 37 | Calc. Stear. 64.25<br>Carbowax 400 45.75 | Calc. Stear. 48<br>Pluronic F68 20<br>$H_2O$ 32 |
| Instron Rheometer | | | | | |

*Observations before sterilization.
**Calcium Stearate used was a very fine particle size lot.
***Subjective Scale: 1–5, 1-best & 5-worst.

TABLE 2

ABSORBABLE BONE WAX
Effects of Cobalt Sterilization on Consistency & Tactile Properties*

| | Wt % | Change in Consistency | Change in Set-up | Oily Surface | Phase Separation | Smeariness | Change in Color | Change in Odor |
|---|---|---|---|---|---|---|---|---|
| | | | | Signs of Separation | | | | |
| Calcium Stearate<br>Deltyl Prime | 64<br>36 | none | none | none | none | same | none | slight enhancement of odor |
| Calcium Stearate<br>Sesame | 63<br>37 | none | none | none | none | same | none | none |
| Calcium Stearate<br>Carbowax 400 | 54.25<br>45.75 | none | none | generated on prolonged exposure to air | none | same | none | none |
| Calcium Stearate<br>Pluronic F68<br>Water | 48<br>20<br>32 | none | stiffens on prolonged exposure to air; set-up & consistency regenerated with work-up | none | none | same | none | none |

*Effect of Cobalt-60 determined by comparing packaged & sterilized samples to similar samples left unsterilized.

TABLE 3

ABSORBABLE BONE WAX
Results of Tissue Reaction to Individual Sterile Components

| Component | Package | Air or $N_2$ | Sterilization $^{60}Co$, mR | Results (ventral subcutis) Rats 1 Day | 7 Days |
|---|---|---|---|---|---|
| Deltyl Prime | vial | $N_2$ | 2.5 | No adverse Tissue Reaction (NATR) slight congestion & edema at periphery of encapsulated fluid. | NATR, small amount of injected fluid remained. |
| Sesame Oil | vial | $N_2$ | 2.5 | | Transparent jelly-like mass on skin side containing clear oil fluid. |
| Carbowax 400 | vial | $N_2$ | 2.5 | No adverse Rxn in live rat. | NATR, no evidence of injected material. |
| Pluronic F68<br>+4–5% $H_2O$ | P.E. sleeve-then foil pouch | Air | 2.5 | Extensive edema, Systemic Effects: lethargic, anal area wet, paws tinged with blood. | NATR, Rats appeared in good health, material completely absorbed. |
| Almond Oil | vial | $N_2$ | 2.5 | | NATR |

TABLE 4

ABSORBABLE BONE WAX
Results of Tissue Reaction to Implanted Bone Wax Compositions

| Composition | Wt. % | Results After 7 Day Implantation (Ventral Subcutis) Rats |
|---|---|---|
| Calcium Stearate | 64 | No adverse tissue reaction, small amount of hemmorrhaging. |
| Deltyl Prime | 36 | No change in consistency or color of bone wax. Thinly encapsulated with small amount of fluid in one rat. |
| Calcium Stearate<br>Sesame Oil | 63<br>37 | No adverse tissue reaction. |
| Calcium Stearate<br>Carbowax 400 | 54.25<br>45.75 | Bone wax encapsulated w/bloody fluid. Bone wax not intact, bone wax not loose, most stuck to the sides of the capsule. |
| Calcium Stearate<br>Pluronic F68 | 48<br>20 | White, creamy, thick capsule. Bonewax dispersed as spongy mass stuck to the sides of capsule. |

TABLE 4-continued
ABSORBABLE BONE WAX
Results of Tissue Reaction to Implanted Bone Wax Compositions

| Composition | Wt. % | Results After 7 Day Implantation (Ventral Subcutis) Rats |
|---|---|---|
| H₂O | 32 | |

Twenty 1 gram samples of each of the 4 candidates were packaged and sterilized for toxicity studies. The packaging involved placing bone wax pellet in polyethylene sleeve (sealed on 3 sides), then inserting the sleeve in a foil pouch and sealing under nitrogen. Fifteen packages received 2.5 Mrads of ⁶⁰Co sterilization while the remaining 5 were kept as a control. All implanted samples were sterile.

TABLE 5
ABSORBABLE BONE WAX
Select Candidates, Summary of Aesthetic, Tissue Reaction & Surgical Use Properties

| Composition | Wt. % | Consistency* | Tissue Reaction to Rats (See Table 5 for Details) |
|---|---|---|---|
| Calcium Stearate | 64 | 3 | NATR, (no adverse tissue reaction) no change in consistency or color of bone wax. |
| Deltyl Prime | 36 | | |
| Calcium Stearate | 63 | 5 | NATR, No change in consistency or color of bone wax. |
| Sesame Oil | 37 | | |
| Calcium Stearate | 54.25 | 4 | Bone wax encapsulated with bloody fluid, bone wax not intact. |
| Carbowax 400 | 45.75 | | |
| Calcium Stearate | 48 | 4 | White, creamy thick capsule. Bone wax dispersed as spongy mass stuck to sides of capsule. Not a favorable reaction. |
| Pluronic F68 | 20 | | |
| H₂O | 32 | | |

*All samples packaged and sterilized, see Table 4.
Scale 1-5, 5 best, 1 worst.

TABLE 6
INTRAMUSCULAR* ABSORPTION OF BONE SEALANT IMPLANTS
(Effect of absorption enhancing agent)

| Absorption Time | Calcium Stearate 60.0%<br>Castor Oil 40.0% | Calcium Stearate 41.4%<br>Dextran 30.0%<br>Castor Oil 28.6 |
|---|---|---|
| One Week | no cell ingrowth<br>little tissue reaction | little tissue reaction<br>most of implant in one piece |
| Two Weeks | implant smaller, intact<br>inflammatory cell area larger | implant breaking up<br>substantial cell growth |
| Four Weeks | implant smaller, intact<br>very small area of inflammatory cells around implant | implant gone<br>small area of inflammatory cells and fat cells remaining |
| Eight Weeks | implant smaller, intact<br>surrounded by inflammatory cells | |
| Twelve Weeks | implant gone<br>area of inflammatory cells left | |
| Handling Qualities | good | good; does not become soft or sticky when wet<br>can feel slight granular nature of Dextran when a thin film is rubbed between bare fingers |

*Cylindrical rods of bone sealant (which had received ⁶⁰Co sterilization), approximately 1 mm. diameter, were implanted intramuscularly in rats via a 16 gauge syringe needle.

Having now described the invention in detail, it should be readily apparent to one skilled in the art that there are various modifications and alterations which may be made without departing from the spirit and scope of the present invention.

We claim:

1. An absorbable hemostatic composition for use in the control of osseous hemorrhage, comprising:
   (i) a component (A) comprising either a biocompatible fatty acid salt alone, which comprises between 45% and 80% by weight based on the weight of the total composition; or a mixture of said fatty acid salt with a biocompatible in vivo absorption enhancing agent, in which said mixture comprises between 35% and 45% by weight of said fatty acid salt based on the weight of the total composition, and between 25% and 35% by weight of said absorption enhancing agent, based on the weight of the total composition; and
   (ii) a component (B) comprising a body absorbable biocompatible base selected from the group consisting of ethylene oxide/proplylene oxide block copolymers, polyethylene glycols and methoxypolyethylene glycols, triglycerides and fatty acid esters, the cation of said fatty acid salt being selected from the group consisting of calcium, magnesium, zinc, aluminum, lithium and barium, the fatty acid anion being saturated or unsaturated and containing from 10 to 22 carbon atoms in the chain, said composition having a putty-like consistency at room temperature, and a tackiness sufficient for it to adhere readily to a bloody bone surface.

2. The composition of claim 1, in which component (A) comprises calcium stearate, calcium palmitate or calcium myristate.

3. The composition of claim 1, in which component (B) is selected from the group consisting of sesame oil, almond oil, castor oil, cottonseed oil, corn oil, olive oil, cod liver oil, safflower oil and soya oil.

4. The composition of claim 1, in which the absorption enhancing agent is selected from the group consisting of dextran, Carbowax, Pluronics, glycerine and propylene glycol.

5. An absorbable hemostatic composition for use in the control of osseous hemorrhage, comprising:
(i) a component (A) consisting of a biocompatible fatty acid salt,
(ii) at least 15% by weight of a component (B) comprising a body absorbable biocompatible base selected from the group consisting of ethylene oxide/propylene oxide block copolymers, polyethylene glycols and methoxypolyethylene glycols, triglycerides and fatty acid esters,
and up to 40% by weight of water, the cation of said fatty acid salt being selected from the group consisting of calcium, magnesium, zinc, aluminum, lithium and barium, the fatty acid anion being saturated or unsaturated and containing from 10 to 22 carbon atoms in the chain; said composition having a putty-like consistency at room temperature and a tackiness sufficient for it to adhere readily to a bloody bone surface.

6. An absorbable hemostatic composition for use in the control of osseous hemorrhage, comprising:
(i) a component (A) comprising a mixture of a biocompatible fatty acid salt with a biocompatible in vivo absorption enhancing agent, in which said mixture comprises between 35% and 45% by weight of said fatty acid salt, based on the weight of the total composition, and between 25% and 35% by weight of said absorption enhancing agent, based on the weight of the total composition;
(ii) at least 20% by weight of a component (B) comprising a body absorbable biocompatible base, selected from the group consisting of ethylene oxide/propylene oxide block copolymers, polyethylene glycols and methoxypolyethylene glycols, triglycerides and fatty acid esters,
and up to 10% by weight of water, the cation of said fatty acid salt being selected from the group consisting of calcium, magnesium, zinc, aluminum, lithium and barium, the fatty acid anion being saturated or unsaturated and containing from 10 to 22 carbon atoms in the chain; said composition having a putty-like consistency at room temperature, and a tackiness sufficient for it to adhere readily to a bloody bone surface.

7. The composition of claim 6, comprising about 38 weight % calcium stearate, about 28 weight % dextran, about 27 weight % castor oil and about 7 weight % water.

8. An absorbable hemostatic composition for use in the control of osseous hemorrhage, comprising:
(i) a component (A) comprising a mixture of calcium stearate and dextran in which said mixture comprises between 35% and 45% by weight of said calcium stearate based on the weight of the total composition, and between 25% and 35% by weight of dextran, based on the weight of the total composition; and
(ii) a component (B) comprising a biocompatible base consisting of a natural or synthetic oil or wax which is soluble in the body,
said composition having a putty-like consistency at room temperature, and a tackiness sufficient for it to adhere readily to a bloody bone surface.

9. The composition of claim 8, in which component (B) is selected from the group consisting of sesame oil, almond oil, castor oil, cottonseed oil, olive oil, cod liver oil, safflower oil and soya oil.

10. An absorbable hemostatic composition for use in the control of osseous hemorrhage, comprising:
(i) a component (A) comprising a mixture of a biocompatible fatty acid salt with a biocompatible in vivo absorption enhancing agent, in which said mixture comprises between 35% and 45% by weight of said fatty acid salt based on the weight of the total composition and between 25% and 35% by weight of said absorption enhancing agent based on the weight of the total composition; and
(ii) a component (B) comprising a biocompatible base, consisting of a natural or synthetic oil or wax which is absorbable in the body, the cation of said fatty acid salt being selected from the group consisting of calcium, magnesium, zinc, aluminum, lithium and barium, the fatty acid anion being saturated or unsaturated and containing from 10 to 22 carbon atoms in the chain; said composition having a putty-like consistency at room temperature, and a tackiness sufficient for it to adhere readily to a bloody bone surface.

11. The composition of claim 10, in which the absorption enhancing agent is selected from the group consisting of dextran, Carbowax, Pluronics, glycerine and propylene glycol.

12. An absorbable hemostatic composition for use in the control of osseous hemorrhage, comprising:
(i) a component (A) consisting of a biocompatible fatty acid salt which comprises between 45% and 80% by weight based on the weight of the total composition; and
(ii) a component (B) comprising a biocompatible base, consisting of a natural or synthetic oil or wax which is absorbable in the body, the cation of said fatty acid salt being selected from the group consisting of calcium, magnesium, zinc, aluminum, lithium and barium, the fatty acid anion being saturated or unsaturated and containing from 10 to 22 carbon atoms in the chain; said composition having a putty-like consistency at room temperature, and a tackiness sufficient for it to adhere readily to a bloody bone surface.

13. An absorbable hemostatic composition for use in the control of osseous hemorrhage, comprising between 35% and 45% by weight of calcium stearate, between 25% and 35% by weight of dextran, the remainder comprising castor oil.

14. The composition of claim 13, comprising about 41 weight percent calcium stearate, about 30 weight percent dextran and about 29 weight percent castor oil.

15. An absorbable hemostatic composition for use in the control of osseous hemorrhage, comprising from 45% to 80% by weight of calcium stearate, and a body absorbable biocompatible base selected from the group consisting of isopropyl palmitate, sesame oil, almond oil, castor oil, ethylene oxide/propylene oxide block copolymers, polyethylene glycols and methoxypolyethylene glycols.

16. The composition of claim 15, in which the calcium stearate comprises between 55% and 70% by weight of the composition.

17. The composition of claim 16, in which the calcium stearate comprises between about 59% and 61% by weight of the composition, and the base is castor oil.

18. A process for the control of bleeding from cut bone surfaces, which comprises applying to the cut bone surface a hemostatic composition comprising
(i) a component (A) comprising either a biocompatible fatty acid salt alone which comprises between 45% to 80% by weight, based on the weight of the total composition; or a mixture of said fatty acid salt with a biocompatible in vivo absorption enhancing agent in which said mixture comprises between 35% and 45% by weight of said fatty acid salt based on the weight of the total composition, and between 25% and 35% by weight of said absorption enhancing agent based on the weight of the total composition; and
(ii) a component (B) comprising a body absorbable biocompatible base, selected from the group consisting of ethylene oxide/propylene oxide block copolymers, polyethylene glycols and methoxypolyethylene glycols, triglycerides and fatty acid esters, the cation of said fatty acid salt being selected from the group consisting of calcium magnesium, zinc, aluminum, lithium and barium, the fatty acid anion being saturated or unsaturated and containing from 10 to 22 carbon atoms in the chain; said composition having a putty-like consistency at room temperature, and a tackiness sufficient for it to adhere readily to a bloody bone surface.

19. The process of claim 18, in which component (B) is selected from the group consisting of isopropyl palmitate, sesame oil, almond oil, castor oil, ethylene oxide/propylene oxide block copolymers, polyethylene glycols and methoxypolyethylene glycols.

20. A process for the control of bleeding from cut bone surfaces, which comprises applying to the cut bone surface a hemostatic composition comprising:
(i) a component (A) comprising a mixture of calcium stearate and dextran in which said mixture comprises between 35% and 45% by weight of said calcium stearate based on the weight of the total composition and between 25% and 35% by weight of dextran based on the weight of the total composition; and
(ii) a component (B) comprising a biocompatible base selected from the group consisting of ethylene oxide/propylene oxide block copolymers, polyethylene glycols and methoxypoly-ethylene glycols, triglycerides and fatty acid esters,
said composition having a putty-like consistency at room temperature, and a tackiness sufficient for it to adhere readily to a bloody bone surface.

21. The process of claim 20, in which component (B) is castor oil.

22. The process of claim 20, in which the composition includes up to 10 weight % of water based on the weight of the total composition, there being present at least 20 weight % of castor oil based on the weight of the total composition.

* * * * *